United States Patent [19]

Huggins et al.

[11] 4,211,762

[45] Jul. 8, 1980

[54] SPECIFIC BINDING ASSAY TECHNIQUES

[76] Inventors: Keith G. Huggins, 44 Berkley Rd., Hillingdon, Middlesex; Ivan M. Roitt, 995 Finchley Rd., London, both of England

[21] Appl. No.: 872,668

[22] Filed: Jan. 26, 1978

[51] Int. Cl.² .................. G01N 33/16; A61K 43/00
[52] U.S. Cl. ............................. 424/1; 23/230 B
[58] Field of Search ................. 424/1; 23/230 B

[56] References Cited

U.S. PATENT DOCUMENTS 3,941,876  3/1976  Marinkovich ................. 421/1

OTHER PUBLICATIONS

Rossi et al., J. of Biol. Chem., vol. 252, No. 2, Jan. 25, 1977, pp. 704–711.

*Primary Examiner*—Benjamin R. Padgett
*Assistant Examiner*—Christine M. Nucker
*Attorney, Agent, or Firm*—James D. McNeil

[57] ABSTRACT

The standardization of a labelled constituent, such as anti-IgE, for use in a specific binding assay method is disclosed. The method involves standardizing a labelled ligand (eg., radiolabelled IgE) against a ligand reference substance (eg., WHO standard IgE) to determine the weight of IgE protein represented by the labelled ligand, expressed in terms of the reference substance (eg., WHO units). Anti-light chain antibodies are attached to a solid phase and contacted with varying concentrations of the labelled ligand to bind the ligand to the anti-light chain antibodies. The ligand is then contacted with the labelled constituent and the amount of labelled constituent, in relation to the amount of ligand protein present, expressed in terms of the reference substance, is determined. The labelled constituent is thus standardized, since the actual weight of a ligand can be determined from the amount of labelled constituent bound thereto.

Also disclosed is an improved specific binding assay test method for determining the potency of an allergen extract. The test method generally involves inhibition by the soluble extract, of the binding of a ligand (provided by serum from an allergic individual) to solid-phase allergen as assessed by the standardized labelled constituent (anti-IgE). The improvement involves using a parallel model system of a second complex which consists of anti-light chain antibodies, labelled ligand and the standardized labelled constituent. Because the actual weight of a ligand bound to the labelled constituent is known, from the standardization procedure described above, the amount of standardized labelled constituent bound to the ligand in the first complex can be determined. The weight of ligand inhibited by addition of soluble allergen is then used as a measure of the potency of the allergen extract.

24 Claims, 5 Drawing Figures

DOUBLE ANTIBODY ASSAY STANDARD CURVE (PLOTTED ON LOGIT V. LOG AXES) FOR THE DETERMINATION OF IgE CONCENTRATION IN WHO UNITS.

DETERMINATION OF ALLERGEN POTENCY

SPECIFIC BINDING ASSAY TECHNIQUES

BACKGROUND OF THE INVENTION

Field of the Invention

Hypersensitive individuals undergo an "altered state" as a result of contact with the antigens from an allergen, leading to the formation of antibodies thereto. Subsequent contact with one of those antigens or a structurally similar substance can evoke in an allergic individual a pathological reaction, due to the presence of such antibodies. When these individuals inhale or ingest the offending antigen, a prominent and common manifestation includes hay fever, asthma or hives. These antibodies are tissue-sensitizing and can be referred to as reagin Ig. There are five classes of antibody; IgE, IgG, IgA, IgM and IgD. IgE constitutes the class of antibodies of major importance in atopic allergy.

In vivo diagnostic tests for atopy, i.e. to determine the presence of IgE produced in response to allergens, are generally conducted by injecting small amounts of the suspected allergen into the skin of the sensitive individual, and examining the injected site for formation on the skin of an irregular wheal surrounded by a zone of erythema. In addition to in vivo tests, in vitro diagnostic tests have been developed. One type of in vitro diagnostic test involves analytical procedures which can be broadly classified as "specific binding assays".

Specific binding assay procedures, with reference to in vitro diagnostic tests for atopy, involve the detection of a ligand in a body fluid. A typical specific binding assay procedure is the determination of IgE antibodies (ligand) in the blood serum of a hypersensitive individual. U.S. Pat. No. 3,720,760 is directed to an in vitro diagnostic test; the technique disclosed by the patentee is commonly referred to as the "RAST" (radioallergosorbent test).

In order to illustrate the scope of the present invention, the RAST technique is decribed herewith in detail. The test involves a first step of attaching a test allergen (antigen) to an insoluble polymeric substrate to form a bound solid-phase antigen. The second step involves contacting the solid-phase antigen with serum from an atopic individual (having IgE antibody present); the IgE is the ligand referred to earlier. The IgE attaches to IgE receptor sites on the antigen, to form an antigen-ligand complex. The third step involves contacting the complex with a labelled constituent, which is a conjugate of a labelling substance and a binding component (capable of binding to the ligand), e.g., radio-labelled anti-IgE.

Various labelling substances can be used. Because of the hazard and difficulty of handling radioactive materials, many new assay systems, which can be designated as "RAST-type" systems, have been devised using materials other than radioactive isotopes as the labelling substance. Examples of labelling substances include free radicals, fluorescent molecules (e.g., fluoroscein isothiocyanate and rhodamine dyes), luminescent molecules, bacteriophages, enzymes, coenzymes and enzyme inhibitors.

Antibodies are normally composed of four chains, two light chains and two heavy chains. In both types of chains there is a constant region and variable region, i.e., the amino acid sequence of the region is relatively constant or varible, respectively. The amino acid sequence of the variable region depends upon the identity of the antigen against which it is directed; the variable region of the antibody molecule that binds the antigen is included within the antibody binding fragment (Fab) obtained by papain digestion. The constant region does not vary with regard to the antigen against which the antibody molecule is directed but is characteristic for a given antibody class. Part of the heavy chain constant region forms the other fragment (Fc) released by papain digestion.

The IgE binds to the antigen via the antibody fragment (Fab) region of the antigen molecule, leaving the Fc region exposed. The radiolabelled anti-IgE then binds to the IgE via the Fc region of the IgE.

The RAST reaction product, is a substrate having attached thereto three "layers": (1) solid-phase antigen; (2) IgE specifically directed against the antigen; and (3) radiolabelled anti-IgE which specifically reacts with IgE. The radiation emitted by the radiolabelled reaction product is a measure of the amount of antigen specific IgE present in the test serum. The use of the RAST described above enables determination of the presence and, to a limited extent, the quantity of IgE present in a patient's serum, capable of reacting with the antigen attached to the substrate. This test in conjunction with skin testing gives an indication as to whether or not the patient is allergic to the antigen.

Following diagnosis of atopy, a common method of treating allergic disorders is by immunizing ("desensitizing") the individual with a course of injections of gradually increasing amounts of allergen extracts. Because of the danger of triggering anaphylactic shock, the amounts of allergen extract administered must be carefully controlled.

Variation in the potency of the allergen extract administered, as indicated by measurement of the reactivity in the skin of sensitive individuals, has been observed. This variation of potency indicates the desirability of improving the standardization of allergen extracts. Difficulties with standardization of allergen extracts is thought to arise because allergen (e.g. pollen) extracts, are usually complex mixtures, and it has been difficult to determine which constituents are responsible for eliciting either an allergic reaction or therapeutic effect during therapy. Methods of expressing potency have been largely indirect and based either on a simple ratio of raw source materials to volume of extracting fluid or on the protein nitrogen of the extract. Since most allergens appear to be proteinaceous in nature, designation of potency by protein nitrogen units (PNU), defined as 0.01 $\mu$g of phosphotungstic acid-precipitable nitrogen, has gained wide acceptance. PNU content however, is not necessarily related to biologic activity, because allergen extracts may contain proteins which are not allergenically active. Furthermore, specific protein allergens may be denatured during extraction or storage, with loss of their biologic activity, yet still appear as protein in a chemical determination.

A second use of binding assay techniques, such as the RAST, is in the measurement of the potency of allergens, in an attempt to standardize allergens for use in diagnostic skin testing and for in vivo desensitization. This utilization is carried out by maintaining the second and third layers (i.e., IgE and labelled anti-IgE respectively) constant, and adding increasing amounts of soluble antigen in the first step. The principle of the technique, is based on a competition between solid and fluid-phase antigens for IgE receptor sites in the first step of the RAST. As the amount of soluble antigen is increased, a smaller amount of IgE complexes with the solid-phase antigen because of the increase in complexes formed between the fluid-phase antigen and IgE. This in turn decreases the percent binding of radiolabelled anti-IgE to solid-phase antigen in the third step of the RAST. This decrease in percent binding of anti-IgE to solid phase antigen produces a decrease in the amount of radiation emitted by the solid-phase.

Starting with 100 percent binding, by careful titration, the quantity of soluble antigen needed to achieve a 50 percent inhibition of the binding can be determined. By plotting the amount of soluble antigen required, against the amount of inhibition produced, on semilog paper, an approximate linear relationship can be established. In particular, between the region of 30 to 70 percent inhibition the semilog plots are reasonably linear. The end point in these titrations can be arbitrarily selected as the amount of allergen extract required for 50 percent inhibition. In theory, comparison of a series of allergen extracts would provide comparative data sufficient to enable standardization of the extracts. [See *J. Allergy Clin. Immunol.* 53; 158–159 (1974)]. As described below, this method suffers from various disadvantages.

One disadvantage lies in the anti-IgE itself. The final reagent used in the RAST, the radiolabelled anti-IgE, is produced by radiolabelling with a radioactive iodide salt. This produces radiolabelled anti-IgE with a half-life sufficiently short to achieve the necessary sensitivity for the measurement of low concentrations of IgE. However, the short half-life means that the radiolabelled anti-IgE is changing rapidly and prevents its use as a standard reference reagent over any reasonable time period. In addition, harsh iodination conditions and subsequent radiation damage during the radiolabelling process produce variations in the radiolabelled anti-IgE. Because of these variations, it is not possible to directly compare two assays performed at different times, using the same batch of radiolabelled anti-IgE or at the same time using different batches of radiolabelled anti-IgE. By standardizing the radiolabelled anti-IgE according to the present invention, these disadvantages are obviated.

Standardization by RAST inhibition suffers other disadvantages. The RAST itself is not a standardized technique. Typically, radioimmunoassays are standardized by the establishment of a stated well-defined reference reagent, either an antigen or antibody. However, allergens are complex mixtures which are not-well defined and their stability is not clearly known. Thus at best this method can only partially standardize the RAST. However, it has been proposed (See *J. Allergy Clin. Immunol.* 53: 158–169, 1974) that serum from atopic individuals could be used as a reference reagent for the more common allergies. This too would only result in a partial standardization of the RAST because serum represents a complex mixture with ill-defined antibody specificities. In spite of the inherent difficulties, ranking of atopic sera for use in the direct RAST has been proposed (See *Advances in Diagnosis of Allergy: RAST* pp. 85–99 Symposium specialists [1975]).

In theory, radiolabelled anti-IgE for the third step of RAST could be standardized by keeping the first and second layers constant and comparing the radiolabelled anti-IgE in the third layer. The standardized radiolabelled anti-IgE could then be used to standardize the RAST test itself. Standardization of anti-IgE RAST with standardized radiolabelled anti-IgE would be useful in that one standard reagent could be used, regardless of the allergen extract present in the first layer. However, because the reagents used in the first two steps of RAST are complex mixtures of ill defined stability, these steps are difficult to reproduce precisely from one experiment to the next. Since it is also difficult to define the activity of samples of radiolabelled anti-IgE precisely, this reagent could not easily be used as a reference standard.

As referred to earlier, an important example of a binding assay employing a labelled compound is radioimmunoassay, such as radioallergosorbent (RAST) techniques. Alternative labelled materials suggested are free radicals, fluorescent molecules, luminescent molecules, bacteriophages, enzymes, coenzymes or enzyme inhibitors. Similar difficulties exist for defining the activity of any labelled material, irrespective of the material against which it is directed or the type of labelled compound used.

DESCRIPTION OF THE PRIOR ART

Ceska and Lundvkist, *Immunochemistry*, 2: 1021–1030, 1972 disclose a three-layer solid phase assay for nonspecific IgE. The first layer is unlabelled anti-IgE; the second layer is the IgE under test; and, the third layer is labelled anti-IgE. This method could not be used to standardize labelled constituents for use in specific binding assay techniques because the solid phase anti-IgE of the first layer partially sterically hinders the subsequent binding of the labelled anti-IgE of the third layer. Steric hindrance occurs when the solid phase anti-IgE of the first layer binds some molecules of IgE in such a way that they are not available for binding the labelled anti-IgE of the third layer. Steric hindrance is undesirable in specific binding assay techniques. The present invention discloses and claims the use of a standardization technique which involves a model system of anti-light chain antibodies in a three-layer solid phase assay system. There is no suggestion or disclosure by the authors of the use of a model system of anti-light chain antibodies for standardization of a labelled constituent such as labelled anti-IgE.

SUMMARY OF THE INVENTION

The present invention is directed to a method of standardizing a labelled constituent which is a conjugate of a first labelling substance and a binding component for use in a specific binding assay method. The present invention is also directed to a procedure for utilizing the standardized labelled constituent in specific binding assay techniques e.g., determination of allergen potency and determination of amount of ligand present in body fluids. The invention includes the following:

1. A method of standardizing a labelled constituent, which is a conjugate of a first labelling substance and a binding component and which is capable of reacting with a ligand, against a ligand reference substance for use in a specific binding assay method which comprises the steps of:

(a) incubating substrates having anti-light chain antibodies bound thereto with varying concentrations of a ligand which is labelled with a second labelling substance, wherein both the amount of ligand protein present in the labelled ligand, represented by the second labelling substance, and the amount of ligand reference substance equivalent to the labelled ligand protein, in terms of the amount of labelled ligand present, are known, for a time sufficient to form a series of products which are substrates having anti-light chain-antibodies attached thereto, and varying amounts of labelled ligand attached to the anti-light chain antibodies;

(b) incubating the products of step (a) with the labelled constituent whereby the labelled constituent is bound to the labelled ligand;

(c) measuring the products of step (b), and determining the amount of the labelled ligand and the labelled constituent;

(d) determining the ligand protein present in the products of step (b), based on the amount of labelled ligand present, by means of the relationship known from (a); and (e) determining in the products of step (b) the amount of ligand protein present, expressed in terms of the ligand reference substance, whereby the labelled constituent is standardized in terms of the ligand bound thereto, for use in a specific binding assay technique.

2. In a specific binding assay test method which involves the reversible non-covalent binding of a ligand and a labelled constitutent which is a conjugate of a first labelling substance and a binding component and which is capable of reacting with the ligand, and wherein the ligand is also bound to an activated substrate, the improvement which comprises the steps of labelling the ligand with a second labelling substance which is different than the first labelling substance of the labelled constituent, whereby the labelled ligand can be distinguished from the labelled constituent, and calibrating the labelled constituent against the labelled ligand, with reference to an appropriately selected ligand reference substance.

DETAILED DESCRIPTION OF THE INVENTION

Figure 1:
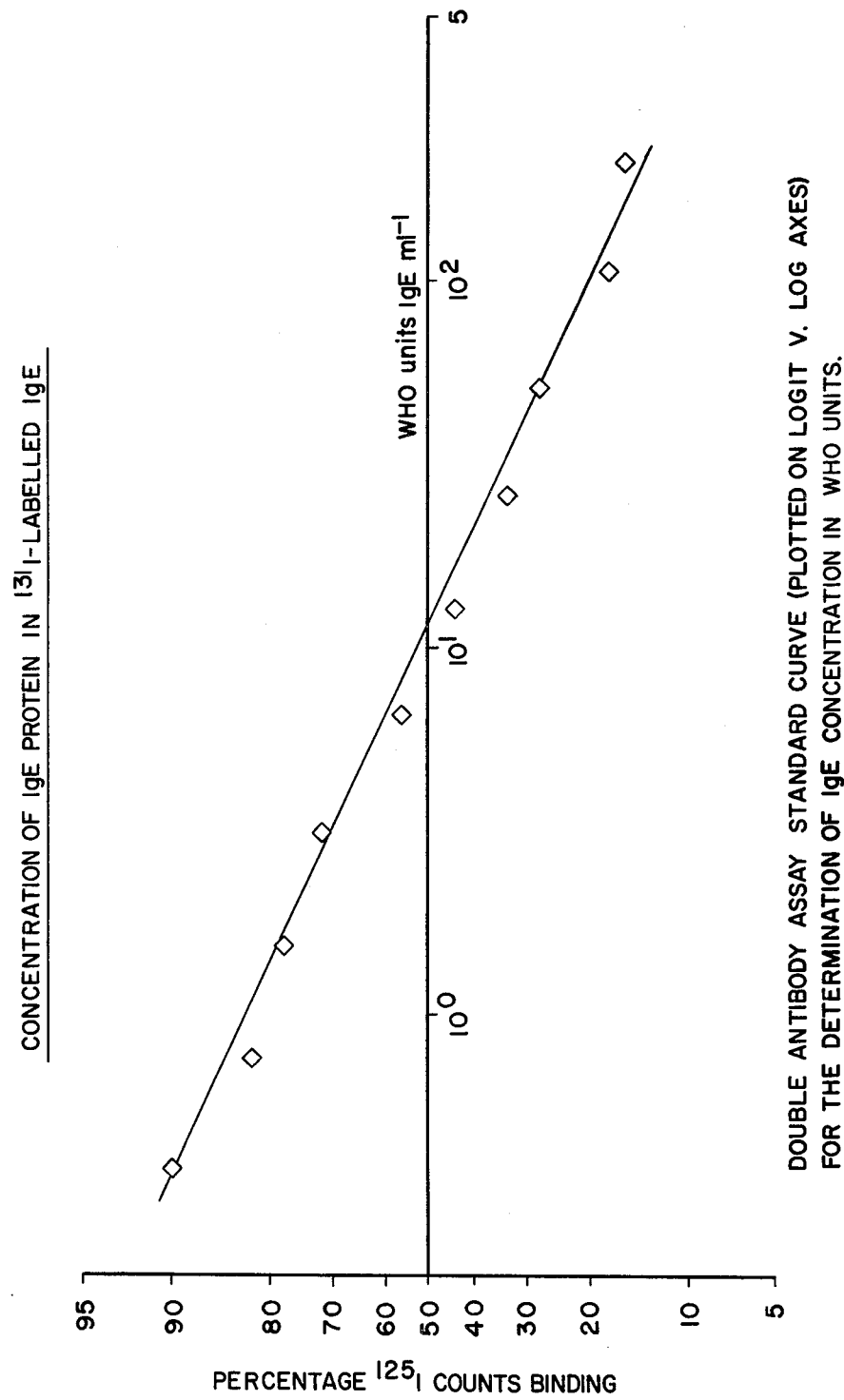
FIG. 1 is a standard curve (plotted on logit v log axes) for the determination of the amount of IgE, expressed in World Health Organization (WHO) units.

The present invention provides a method for standardization of a labelled constituent. According to the invention, a labelled constituent, such as anti-Ig, is standardized in terms of an internationally or nationally recognized refernce Ig, expressed as international or national units. The standardized labelled anti-Ig can be used in specific binding assays. For example, standardized labelled anti-IgE can be used in specific binding assay procedures, such as in radioallergosorbent procedures, (RAST) for standardizing allergen extracts (antigens). The standardized labelled anti-Ig can also be used for determining the amount of Ig antibodies present in body fluids, eg., IgE antibodies present in atopic serum.

As discussed hereinbefore, antibody molecules contain antigen-binding properties in the end of the molecule designated as the antigen-binding fragment (Fab), which are specific with regard to binding specific antigens. The other end of the molecule, designated as Fc, does not bind antigens.

In specific binding assay methods involving radioisotopes, IgE antibodies bind to antigen via the Fab portion, leaving the Fc portion exposed. During the second incubation with the radiolabelled anti-IgE, the anti-IgE binds to the exposed Fc portion of the IgE molecule. In order to function properly in these tests, the labelled anti-IgE must be standardized in a way that closely simulates the activity of the labelled anti-IgE in the test. This "simulation" requirement means that, since the specific binding assay technique, e.g., RAST, or techniques using other labelling substances such as enzymes, are relatively sterically unhindered, the procedures used to standardize labelled anti-IgE should also be relatively sterically unhindered, The disclosed and claimed standardization procedure, using anti-light chain antibodies bound to an activated substrate, meets this simulation requirement.

The method of the present invention is, in its broadest aspect, directed to standardization of a labelled constituent and the utilization of the labelled constituent in specific binding assay techniques. As discussed hereinbefore, various labelled substances can be used in specific binding assay techniques. Preferred embodiments include radioisotopes and enzymes. The labelled constituent can be utilized in all three-layer specific binding assay techniques. Preferred embodiments of utilization include standardization of allergen extracts and determination of, or detection of, a ligand in a body fluid. Such ligands include antibodies, e.g., Ig, and proteins. A preferred embodiment is the detection of, or determination of, IgE in atopic serum.

In the standardization procedure of the preferred embodiment, radiolabelled anti-IgE is standardized against IgE. The IgE in turn is standardized against IgE reference standard. The IgE reference standard described in the preferred embodiment is standard IgE reference serum, obtained from the World Health Organization (WHO) and is designated as IgE (69/341), containing 10,000 WHO units per ml.

DESCRIPTION OF THE PREFERRED EMBODIMENT

The RAST, as described earlier, is an example of a triple-layer solid phase assay technique utilizing radioisotopes. In order to simulate specific binding assay techniques, e.g., the RAST procedure, a procedure to standardize the labelled anti-IgE for use in a specific binding assay technique must simulate the assay technique. Since the RAST is relatively sterically unhindered, a method for standardizing anti-IgE for use in a specific binding assay technique must also be relatively sterically unhindered. The standardization procedure of the present invention utilizes a triple-layer solid phase assay technique, in which the first layer is anti-human light chain antibody bound to the insoluble support. The second layer is labelled IgE. The third layer is labelled anti-IgE. The labelled IgE is distinguishable from the labelled anti-IgE being standardized.

The claimed method for standardizing labelled anti-IgE and the claimed method for determining the potency of an antigen is described below.

Procedure for Standardizing Radiolabelled Anti IgE

As described in A, IgE was radiolabelled with Na$^{131}$I. The radiation emitted was measured. The relationship between the radiation emitted by the $^{131}$I radiolabelled IgE and the amount of the IgE protein present in the radiolabelled IgE, was determined as described below by the double antibody method of Gleich et. al., [*J. Lab. Clin. Invest.* 77: 690–698 (1971)] after reference to a standard curve constructed using the WHO IgE reference serum such that the concentration of radiolabelled IgE protein is expressed in WHO units.

The standard curve is established by the double antibody method using a fluid-phase competitive inhibition of a reaction between $^{125}$I radiolabelled IgE and unlabelled rabbit anti-IgE by increasing concentrations of the WHO IgE reference serum. The $^{131}$I radiolabelled IgE replaced the WHO reference serum in the inhibition assay. The ability of the $^{131}$I radiolabelled IgE to inhibit the binding of $^{125}$I radiolabelled IgE to the unlabelled rabbit anti-IgE was compared, by reference to the standard curve, with the inhibitor ability of the WHO IgE reference serum in the same assay and the concentration of IgE in the $^{131}$I radiolabelled IgE preparation established.

Iodine-125 radiolabelled IgE, commercially available from Pharmacia, London, was reacted with unlabelled anti-IgE, commercially available from Behringwerke A.G. in the presence of increasing amounts of WHO. IgE reference serum to form a series of $^{125}$I-radiolabelled IgE-anti-IgE complexes. Since it is necessry to separate these complexes from the soluble unreacted $^{125}$I radiolabelled IgE they were precipitated by addition of donkey antirabbit immunoglobulin serum, commercially available from Wellcome Laboratories.

The radiation emitted by the $^{125}$I radiolabelled IgE present in the series of complexes was determined and a standard curve constructed. The concentration of IgE protein contained in the $^{131}$I IgE preparation was determined from the standard curve directly in WHO units, correcting the $^{125}$I values for counts overlapping from the $^{131}$I isotope. A standard curve (plotted on logit v. log axis), for the determination of the quantity of IgE in WHO units, is shown in FIG. 1. Prior to adding WHO IgE reference serum, the binding reaction between $^{125}$I radiolabelled IgE rabbit anti-IgE can be considered as 100 percent. According to FIG. 1, at 50 percent inhibition of binding, slightly greater than $10^1$ WHO units IgE ml$^{-1}$ has been added to the complexes.

The double antibody assay described above gave the following results. A $^{131}$I radiolabelled IgE preparation was found to contain 224 WHO units IgE ml$^{-1}$ (22.4μ IgE 0.01 ml$^{-1}$). Radiation emitted by a sample of $^{131}$I IgE was determined to be equivalent to 450,000 cpm. The response for each unit of IgE contained in the radiolabelled preparation was calculated to be 20,000 cpm.

Alternatives to the double antibody method of Gleich for determination of IgE quantity in WHO units can be used, such as the method of Ceska and Lundvkist (*Immunochemistry*, 2: 1021–1030, 1972).

As described in B, anti-IgE was radiolabelled with $^{125}$I. The radiation emitted from the anti-IgE was distinguishable from the radiation emitted from the $^{131}$I radiolabelled IgE. The identity of the radioactive isotopes is not important, as long as the radioactivity is distinguishable.

Activated substrates in the form of discs were contacted with anti-human light chain antibodies as described in D. The discs were then incubated with varying concentrations of the $^{131}$I radiolabelled IgE for about 3 hours at 20° C. The excess reagents were removed and the discs washed four times with 1 percent detergent in saline, e.g., "TWEEN", commercially available from Sigma Chemical, St. Louis, Missouri. The discs were then incubated for about 17 hours with the $^{125}$I radiolabelled anti-IgE, to form a substrate having attached thereto the triple-layer solid phase product illustrated in the preceding drawing.

Figure 2:
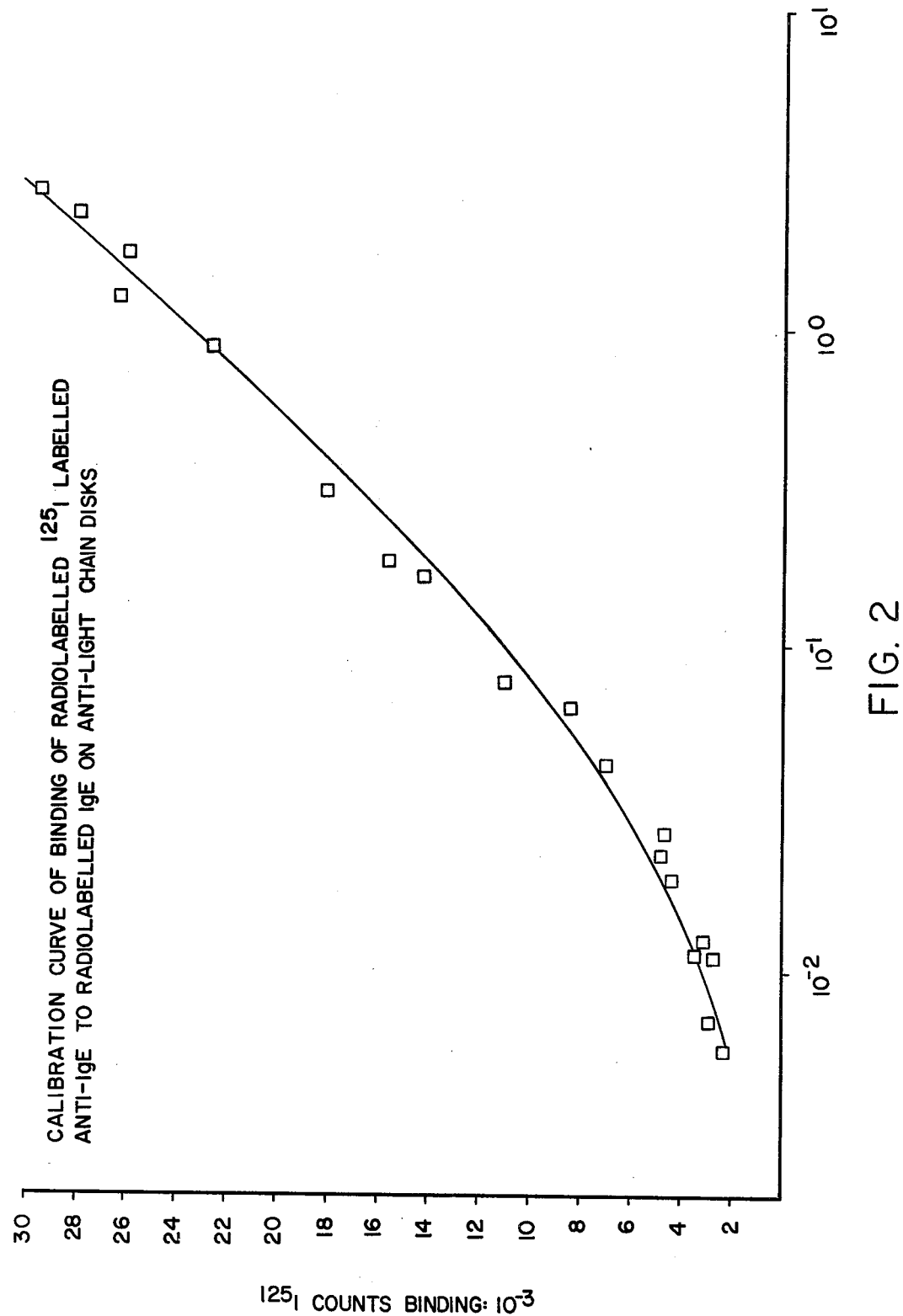
FIG. 2 is a calibration curve of binding of $^{125}I$ labelled anti-IgE to IgE on anti-light chain discs.

After washing, the radioactivity of the $^{131}$I IgE and the $^{125}$I anti-IgE was counted simultaneously in a gamma counter. The amount of IgE protein in the $^{131}$I radiolabelled IgE, expressed directly in WHO IgE units, in relationship to the $^{131}$I radioactivity emitted was previously determined. The $^{125}$I anti-IgE counts, corrected for an overlap of $^{131}$I counts, were plotted against the units of IgE bound to the discs, as determined from the $^{131}$I counts. This gave a calibration curve, shown in FIG. 2, from which IgE bound to an activated disc can be related to the subsequent binding of radiolabelled anti-IgE. Therefore, the relationship between the amount of radiation emitted by the radiolabelled anti-IgE, the amount of IgE protein attached to radiolabelled anti-IgE and the amount of IgE protein, in WHO units, is known. By the method of the present invention, as described above, the radiolabelled anti-IgE is standardized in terms of WHO units, since the actual weight of a ligand (eg. IgE) can be determined from the amount of labelled constituent bound thereto.

The standardized radiolabelled anti-IgE can be utilized in the various modifications of specific binding assay techniques referred to earlier, to determine the amount of IgE bound to an activated substrate, regardless of the labelled substance used. The specific embodiment described below is directed to an improved specific binding assay method for the measurement of the potency of an allergen extract. The potency is measured by radioallergosorbent inhibition.

PREPARATION OF MATERIALS FOR STANDARDIZING RADIOLABELLED ANTI-IgE

A. Radiolabelled IgE.

Purified IgE (containing less than 0.6% IgG) was prepared by ion exchange and gel chromatography from IgE myloma serum. The IgE was radiolabelled with Na$^{131}$I, available from Radiochemical Centre, Amersham, Bucks, England. The radialabelling was carried out by adding about 0.025 ml of 0.5 M phosphate buffer (pH=7.5) to a 10 μl portion of Na$^{131}$I in a vial. Immediately thereafter 5 μg of IgE in 0.025 ml 0.05 M phosphate buffer and 100 μg of fresh sodium p-toluenesulfochloroamine, available as Chloramine T, available from Sigma Chemical, in 0.025 ml 0.05 M phosphate buffer were added. After each addition, the contents of the vial were mixed. Immediately after adding the toluene sulfochloramine, a 0.1 ml portion of sodium metabisulfite solution (2.4g/ml) in 0.05 M phosphate buffer was added to prevent subsequent iodination. The unreacted reagents were removed by passage through Sephadex G50. The labelled IgE peak was collected and adjusted to 5 ml with 5% human serum albumin in phosphate buffer saline (PBS) and stored at 20° C. [See Biochem. J. 89: 114–123 (1963)].

B. Radiolabelled Anti-IgE.

Sheep anti-human IgE was purified by isolation of the 7S peak from a G200 chromatography column. The specific anti-IgE was eluted with a glycerin/HCl buffer (pH=2.6).

A 10 μg portion of this anti-IgE preparation was radiolabelled with 1 mCi of $Na^{125}I$, available from Radiochemical Centre, Amersham, Bucks, England by the following method.

The labelling procedure was conducted at 4° C. using precooled reagents in an ice bath. A 100 μg portion of purified sheep anti-IgE contained in 100 μl of 0.1 M phosphate buffer (pH 7.0) was placed in a vial and to this added ImCi of $Na^{125}I$ followed immediately by 50 μg of Chloramine T contained in 50 μl of 0.1 M phosphate buffer (pH 7.0). The contents of the vial were mixed and the reaction continued for 30 minutes with intermittant mixing at 4° C. The iodination mixture was neutralized by the addition of 20 μg sodium metabisulphite contained in 5 μl 0.1 M phosphate buffer (pH 7.0). The contents of the vial were mixed and the reaction mixture allowed to stand for a further 5 minutes at 4° C. Five μl of 5 percent bovine serum albumin (BSA) solution were added and the contents of the vial were applied to a Sephadex G50 column where the unreacted reagents were separated. The radiolabelled protein peak was collected and adjusted to 5 ml with 5 percent (BSA) in phosphate buffered saline solution (PBS) and stored at −20° C.

Before use, the anti-IgE preparation was diluted in PBS containing 20% normal sheep serum, 0.2% bovine serum albumin and 1% detergent to give a working solution yielding $10^6$ counts per minute per ml. [See Immunochem. 7: 885–898 (1970)]

C. Activated Substrate

Paper discs (5mm diameter) were punched from filter paper and activated with cyanogen bromide as follows. Suitable filter paper is commercially available from Whatman Biochemical, designed as Whatman No. 54. The substrates, designated "discs", were soaked for about 30 minutes in distilled water, and an aqueous 5% BrCN solution was added. The mixture was placed in a water bath at a temperature of about 20° C. and stirred for about 5 minutes. During stirring, the pH was maintained within the range 10.5–11.0 by dropwise addition of 2 M NaOH. The mixture was poured into about 2 liters of 0.005M $NaHCO_3$ solution at 4° C., and further mixed. The supernatant was decanted, and the discs washed repeatedly with 0.005M $NaHCO_3$ at 4° C., then washed with 500 ml portions of acetone (4° C.), air dried and stored at −20° C.

D. Anti-Human Light Chain Antibodies Coupled to Activated Substrate

Antibodies are made up of chains of peptides, designated as light chains and heavy chains. Light chains have a molecular weight of approximately 20,000; heavy chains have a molecular weight of approximately 50,000. Although light chains of purified antibodies are highly heterogeneous, light chains of myeloma proteins (lymphoid tumor of the human bone marrow) are homogeneous. Patients suffering from myelomas excrete a uniform, homogeneous protein called Bence-Jones protein which are homogeneous light chains.

Anti-human light chain antibodies were prepared and coupled to the activated substrates of C as described below. Antibodies specific to Bence-Jones protein were purchased from Dako, Denmark as an immunoglobulin fraction of a rabbit antisera. The anti-human light chain antibodies were coupled to the activated substrates of C by incubating the antibodies with the substrates for about 1 hour at about 5° C.

The unreacted groups were blocked with β-ethanolamine solution by adding about 1 ml β-ethanolamine solution (0.05 M in 0.1 M $NaHCO_3$). The mixture was agitated in a mechanical shaker (100 r.p.m.) for 3 hours. The solution was removed, and the discs were successively washed with one 2.5 ml portion of 0.1 M $NaHCO_3$, three 2.5 ml portions of 0.1 M acetate buffer (pH=4.0) and three 7.5 ml portions of PBS. The anti-light chain discs were used directly after their preparation.

E. WHO IgE Reference Serum

The serum is available from the World Health Organization. The reference serum used herein was designated as IgE (69/341), containing 10,000 WHO units (U) per ml.

IMPROVED SPECIFIC BINDING ASSAY METHOD

Preparation of Materials

F. Antigen (allergen) Extracts

Allergen extracts of two batches of *Dactylis glomerata* pollen, (Cocksfoot/Orchard) (F/75 and M/76) were obtained from the Manufacturing Division of Miles Laboratories, Bridgend, as freeze-dried preparations and stored at −20° C.

G. Substrate-Antigen

The pollen extract M/76 of F was coupled to the activated substrate of C as follows.

A 4 g portion of the freeze-dried pollen extract was reconstituted to 1 liter with phosphate-buffered saline (pH=7.2). The allergen extract was bound to the activated paper discs as follows. About 100 gm of activated paper discs (approximately 50,000 discs) were incubated with the 4 g reconstituted pollen extract with mechanical mixing for about 20 hours. The unreacted pollen extract solution was removed by decantation. The unreacted groups were blocked with 1 liter of 0.05 M β-ethanolamine for 3 hours. After blocking, the discs were successively washed with a 1 liter portion of 0.1 M $NaHCO_3$, three 1 liter portions of 0.1 M acetate buffer (pH 4.2) and four 1 liter portions of PBS. The washed discs were aliquotted into 0.5 g lots and freeze-dried before storing at −20° C.

H. Atopic Sera

A working dilution of the serum to be used as a source of IgE was selected to provide the desired IgE binding, for use in the allergen potency determination as follows. Serial dilutions of the atopic sera were incubated with a series of activated substrates with antigen attached thereto (prepared as described in G). After washing with a 1 percent detergent solution in saline, the discs were incubated with diluted radiolabelled anti-IgE, prepared as described in the standardization procedure. The product formed was an activated substrate with antigen; IgE and radiolabelled anti-IgE attached.

A parallel incubation was commenced with anti-light chain activated discs. The earlier procedure described, set forth below, was followed to obtain a calibration curve in which the radioactive counts of the radiolabelled anti-IgE were plotted against the units of IgE bound to the discs, as determined from the radioactive counts of the radiolabelled IgE. The anti-light chain activated discs, having radiolabelled $^{131}I$ IgE attached thereto (prepared as described in D) were incubated with the radiolabelled anti-IgE. After washing, the radiation emitted from the discs was counted in a gamma counter. As explained below, a dose response curve was prepared to select the working dilution of each serum which provided the desired IgE binding.

The titration of 3 sera was carried out. One sera consisted of a pool of sera from 30 defined atopic patients, all sensitive to grass pollen. The second and third were obtained from individual subjects, designated M.D. and C.W., both of whom were allergic to grass pollen.

Figure 3:
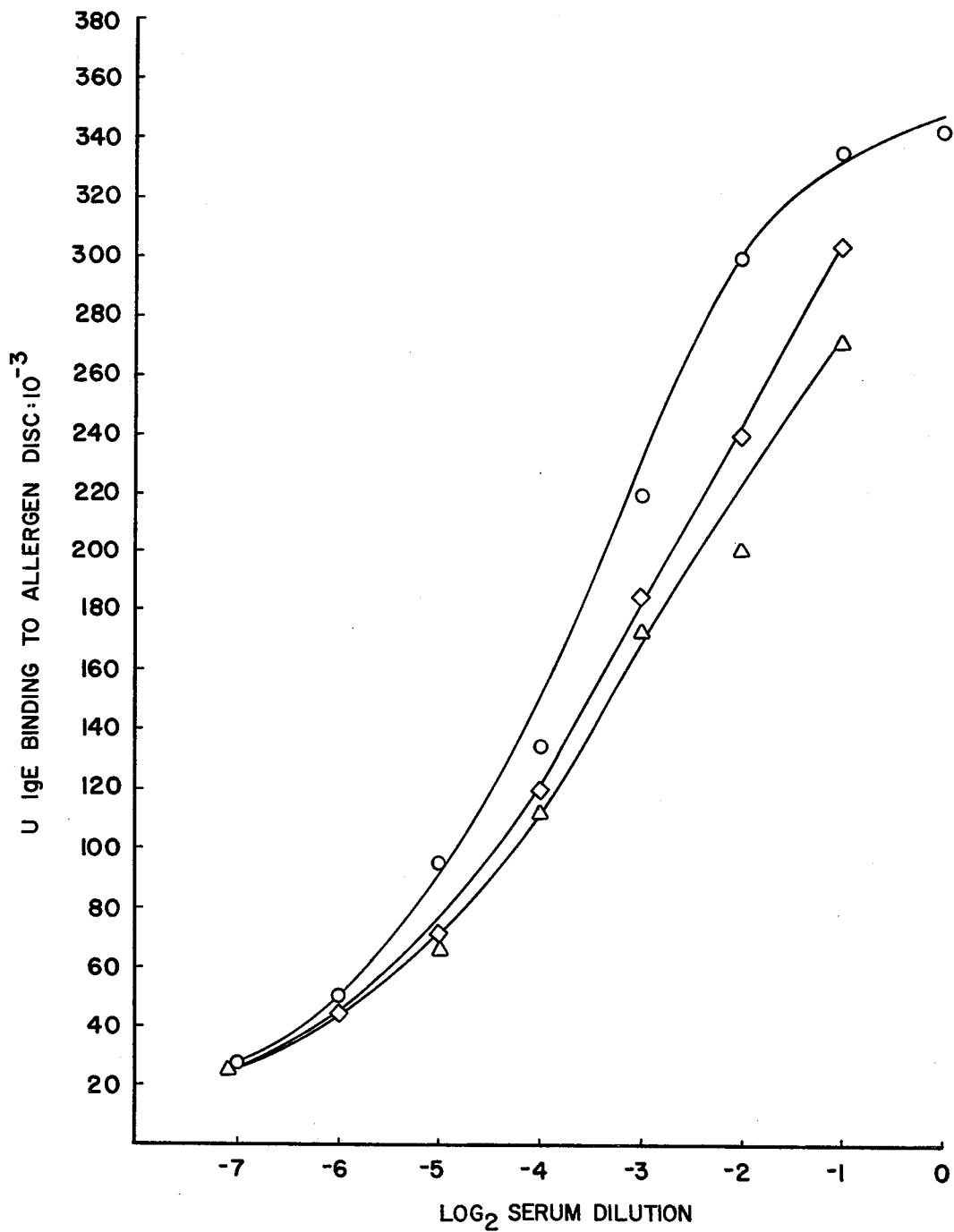
FIG. 3 is a graphic representation of the titration of atopic sera on allergen discs to determine serum working dilution. Operation capacity of the disc ($\Delta$) is $170 \times 10^{-3}$ U IgE)

In order to obtain correct results as to inhibition, the concentration of patient serum (IgE source) must be less than the concentration which would saturate the activated substrate. To determine the concentration of the serum to be employed, different atopic sera were titrated with activated substrates. A family of curves for the IgE binding was obtained, as illustrated in FIG. 3. The dilution required was obtained by determining the concentration which provided an arbitraily defined standard level of IgE binding, designated as the activated substrate capacity; $\Delta$. This $\Delta$ is usually of the order of 50 to 70 percent of the maximium binding of the substrate; in the present invention, $\Delta$ is defined as being $170 \times 3^{13}$ U (WHO units) IgE because this was found to be the optimal level for the performance of the work.

Procedure for Determining Allergen Potency

The determination of the potency of the *Dactylis glomerta* allergen was accomplished as described below. The allergen extracts of (F) were reconstituted in 1 ml of incubation buffer (1 percent BSA) 1 percent detergent in PBS and serially diluted in the buffer. A 100 μl portion of the diluted extract was incubated with a 0.1 ml portion of atoptic serum for 2 hours at 20° C. in trays. The atopic sera was suitably diluted as described hereinbefore, such that the serum concentration was below the concentration required for saturation of the activated disc. A substrate antigen (disc) as prepared in G was added to the serum-allergen reaction mixture, and incubated with the mixture for a further 3 hours. Liquid reagents were aspirated and the substrate antigen-IgE product washed with four 1 ml portions of 1 percent detergent saline. The standardized radiolabelled anti-IgE was then added to the substrate antigen-IgE product to form a three-layer solid phase product. The radiation emitted by the radiolabelled anti-IgE was then measured, and the counts emitted converted to the weight of IgE binding to the anti-IgE by reference to the calibration curve of FIG. 2.

Activated substrates were incubated with anti-light chain antibodies as described in D. The discs were then incubated with varying concentrations of the radiolabelled IgE for about 3 hours at 20° C. The excess reagents were removed and the discs washed four hours with 1 percent detergent in saline. The discs were then incubated for about 17 hours with the radiolabelled anti-IgE (prepared as described in B).

As described hereinbefore, from the assay of radiolabelled IgE, correlated with the WHO IgE reference serum, a standard curve was constructed. (See FIG. 1) This curve was used to calculate the concentration of IgE present in the radiolabelled IgE. Using a known concentration of radiolabelled IgE, the exact amount of IgE binding to anti-light chain discs was then calculated from the radiation emitted. Since the amount of IgE bound is known, the $^{125}$I counts of the radiolabelled anti-IgE bound by the subsequent incubation with radiolabelled anti-IgE can be correlated with the exact amount of radiolabelled IgE present and a calibration curve prepared. (See FIG. 2)

As described and illustrated earlier with the RAST method, in the specific binding assay inhibition test methods, as the amount of soluble antigen added to a solid-phase activated substrate-antigen-IgE complex increases, the weight of IgE molecules bound to the solid-phase antigen decreases, and the percent of binding of anti-IgE to solid phase antigen (via the IgE) decreases. Allergen extracts can then be compared for relative potency by obtaining and comparing the amount of extract required for 50 percent inhibition.

Figure 4:
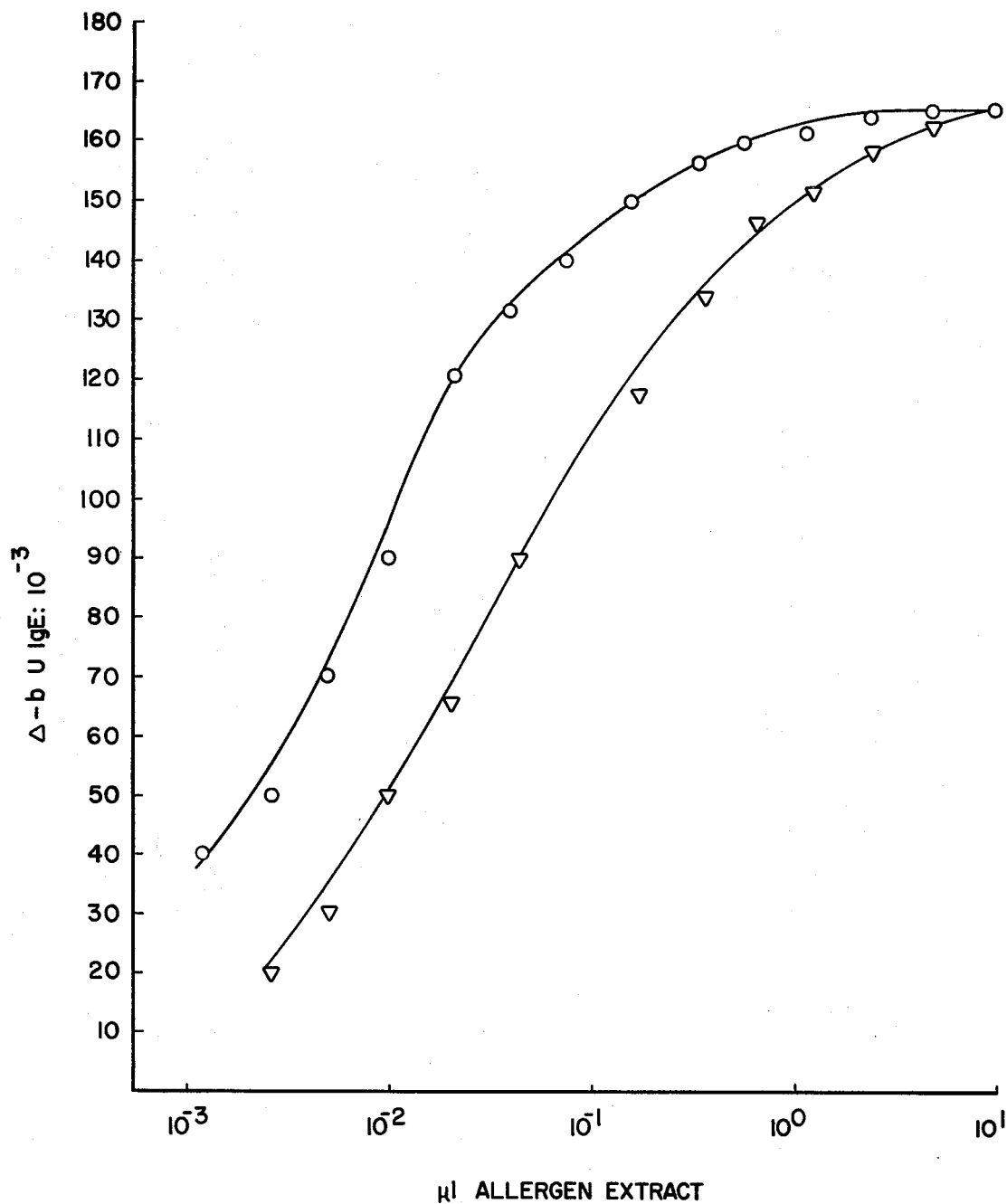
FIG. 4 is a graphic representation of the titration of two different allergen extracts by specific binding assay inhibition, using an atopic serum. ($\Delta = 170 \times 10^{)3}$ U IgE)
Figure 5:
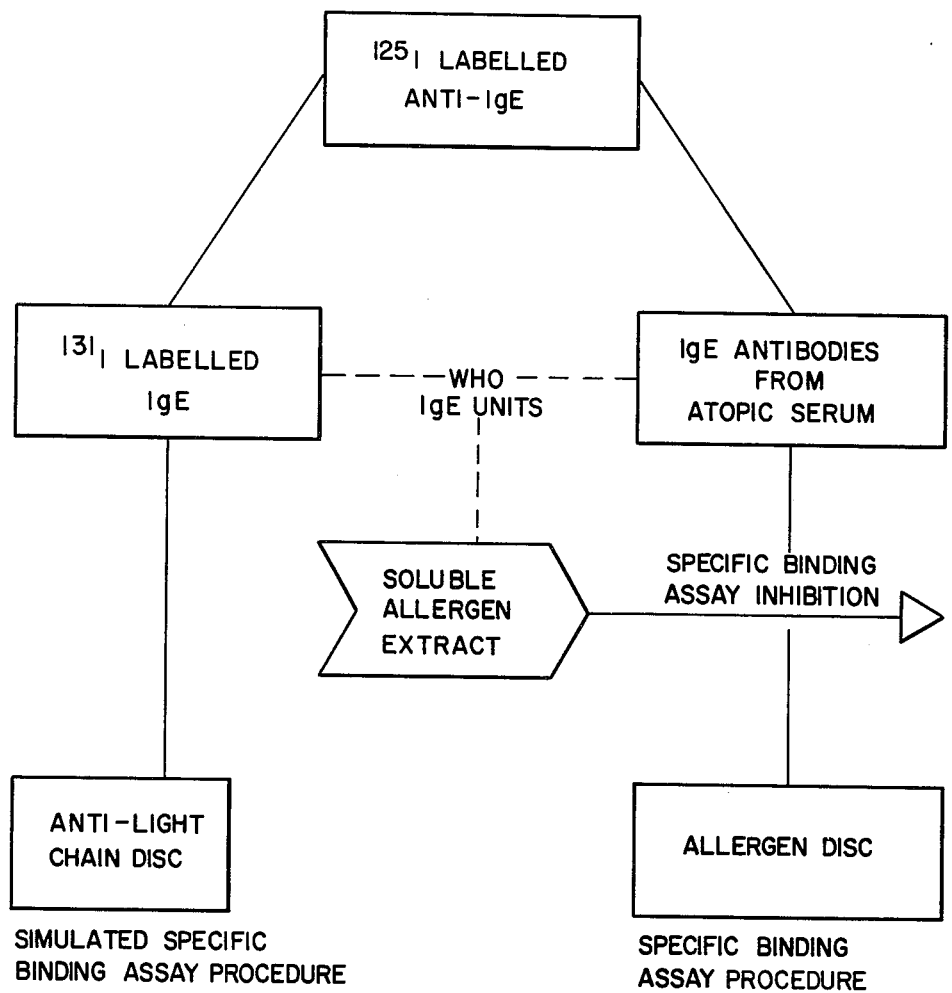
FIG. 5 is a schematic illustration showing the determination of allergen potency according to the present invention.

In the method of the present invention described above, since the disc capacity for binding IgE is designated as $\Delta$, if the bound IgE molecules are designated as b, at any given concentration of allergen, the weight of IgE prevented from binding is therefore given by the expression $\Delta$-b. At some concentration of allergen, the binding of the IgE to the disc to completely inhibited by the presence of the allergen extract. FIG. 4 shows that as the amount of allergen extract added increases, the amount of IgE prevented from binding ($\Delta$-b) also increases.

FIG. 4 illustrates that the maximum amount of antibodies prevented from binding, by the increasing amounts of allergen extract added, is in the vicinity of $170 \times 10^{-3}$ U IgE. Therefore, the titration of a given serum by use of the standarized labelled anti-IgE, according to the present invention, allows one to express the allergen potency, in terms of inhibition of binding, as standard units of IgE, i.e., U IgE.

What is claimed is:

1. A method of standardizing a labelled constituent, which is a conjugate of a first labelling substance and a binding component and which is capable of reacting with a ligand, against a ligand reference substance for use in a specific binding assay method which comprises the steps of:
   (a) incubating substrates having anti-light chain antibodies bound thereto with varying concentrations of a ligand which is labelled with a second labelling substance, wherein both the amount of ligand protein present in the labelled ligand, represented by the second labelling substance, and the amount of ligand reference substance equivalent to the labelled ligand protein, in terms of the amount of labelled ligand present, are known, for a time sufficient to form a series of products which are substrates having anti-light chain-antibodies attached thereto, and varying amounts of labelled ligand attached to the anti-light chain antibodies;
   (b) incubating the products of step (a) with the labelled constituent whereby the labelled consititunent is bound to the labelled ligand;
   (c) measuring the products of step (b), and determining the amount of the labelled ligand and the labelled constituent;
   (d) determining the ligand protein present in the products of step (b), based on the amount of labelled ligand present, by means of the relationship known from (a); and
   (e) determining in the products of step (b) the amount of ligand protein present, expressed in terms of the ligand reference substance, whereby the labelled constituent is standardized in terms of the ligand bound thereto, for use in a specific binding assay technique.

2. A method as claimed in claim 1 wherein the first and second labelling substances are selected from the group consisting of radioisotopes, free radicals, fluorescent molecules, luminescent molecules, bacteriophages, enzymes, coenzymes and enzyme inhibitors.

3. A method as claimed in claim 2 wherein the labelling substances are radioisotopes.

4. A method as claimed in claim 1 wherein labelled anti-Ig is standardized against Ig reference serum.

5. A method of standardizing a labelled constituent which is a conjugate of a first labelling substance and a binding component and which is capable of reacting with a ligand, against a ligand reference substance for use in a specific binding assay method which comprises the steps of:
   (a) reacting a ligand with a second labelling substance which is different than the first labelling substance, for a time sufficient to label the ligand, whereby the labelled ligand can be distinguished from the labelled constituent, and separating therefrom unreacted ligand;
   (b) determining the amount of ligand protein present in the labelled ligand represented by the second labelling substance;
   (c) determining the amount of the ligand reference substance equivalent to the labelled ligand protein, in terms of the amount of labelled ligand present;
   (d) incubating a series of activated substrates with anti-light chain antibodies for a time sufficient to form a series of products which are substrates having anti-light chain antibodies bound thereto;
   (e) incubating the products of step (d) with varying concentrations of the labelled ligand of step (a) for a time sufficient to form a series of products which are substrates having varying amounts of anti-light chain-antibodies attached thereto, and varying amounts of labelled ligand attached to the anti-light chain antibodies;
   (f) incubating the products of step (e) with the labelled constituent whereby the labelled constituent is bound to the labelled ligand;
   (g) measuring the products of step (f), and determining the amount of the labelled ligand and the labelled constituent;
   (h) determining the ligand protein present in the products of step (f), based on the amount of labelled ligand present, by means of the relationship determined in (b); and
   (i) determining in the products of step (f) the amount of ligand protein present, expressed in terms of the ligand reference substance whereby the labelled constituent is standardized in terms of the ligand bound thereto, for use in a specific binding assay technique.

6. A method of standardizing a radiolabelled constituent which is a conjugate of a first radioisotope and anti-IgE and which is capable of reacting with IgE, against IgE reference substance for use in a specific binding assay method which comprises the steps of:
   (a) incubating substrates having anti-light chain antibodies bound thereto with varying concentrations of IgE which are labelled with a second radioisotope, wherein both the amount of IgE protein present in the labelled IgE, represented by the second labelling substance, and the amount of IgE reference substance equivalent to the labelled IgE protein, in terms of the amount of labelled IgE present, are known, for a time sufficient to form a series of products which are substrates having varying amounts of anti-light chain-antibodies attached thereto, and varying amounts of labelled IgE attached to the anti-light chain antibodies;
   (b) incubating the products of step (a) with the labelled constituent whereby the labelled constituent is bound to the labelled IgE;
   (c) measuring the products of step (b), and determining the amount of the labelled IgE and the labelled constituent;
   (d) determining the IgE protein present in the products of step (b), based on the amount of labelled IgE present, by means of the relationship known from (a); and
   (e) determining in the products of step (b) the amount of IgE protein present, expressed in terms of the IgE reference substance, whereby the labelled constituent is standardized in terms of the IgE bound thereto, for use in a specific binding assay technique.

7. A method of standardizing a radiolabelled constituent which is a conjugate of a first radioisotope and anti-IgE and which is capable of reacting with IgE, against IgE reference substance for use in a specific binding assay method which comprises the steps of:
   (a) reacting IgE with a second radioisotope which is different than the first radioisotope for a time sufficient to radiolabel the IgE whereby the radiolabelled IgE can be distinguished from the radiolabelled anti-IgE, and separating therefrom unreacted IgE;
   (b) determining the amount of IgE protein present in the radiolabelled IgE, represented by the radioactivity count;
   (c) determining the amount of the IgE reference substance equivalent to the radiolabelled IgE protein, in terms of the amount of radiolabelled IgE present;
   (d) incubating a series of activated substrates with anti-light chain antibodies for a time sufficient to form a series of products which are substrates having anti-light chain antibodies bound thereto;
   (e) incubating the products of step (d) with varying concentrations of the radiolabelled IgE of step (a) for a time sufficient to form a series of products which are substrates having anti-light chain-antibodies attached thereto, and varying amounts of radiolabelled IgE attached to the anti-light chain antibodies;
   (f) incubating the products of step (e) with the radiolabelled anti-IgE whereby the radiolabelled anti-IgE is bound to the radiolabelled IgE;
   (g) measuring the radioactivity of the products of step (f) and determining the radioactive counts contributed by the IgE and anti-IgE respectively
   (h) determining the IgE protein present in the products of step (f) based on the amount of radiolabelled IgE present, by means of the relationship determined in (b); and
   (i) determining in the products of step (f), the amount of IgE protein present, expressed in terms of the IgE reference substance, whereby the radiolabelled anti-IgE is standardized in terms of the IgE bound to the radiolabelled anti-IgE, for use in a specific binding assay technique.

8. A method as claimed in claim 7 wherein the first radioisotope is $Na^{125}I$.

9. A method as claimed in claim 7 wherein the second radioisotope is Na$^{131}$I.

10. A method as claimed in claim 7 wherein the IgE reference substanbce is World Health Organization reference serum.

11. A method as claimed in claim 10 wherein in step (b), the amount of IgE protein present in the radiolabelled IgE is determined by double antibody competitive inhibition of the IgE reference serum.

12. In a specific binding assay test method which involves the binding of a ligand and a labelled constituent which is a conjugate of a first labelling substance and a binding component, and wherein the ligand is also bound to an activated substrate, the improvement which comprises the steps of labelling the ligand with a second labelling substance which is different than the first labelling substance of the labelled constituent, whereby the labelled ligand can be distinguished from the labelled constituent, and calibrating the labelled constituent against the labelled ligand, with reference to an appropriately selected ligand reference substance.

13. A method as claimed in claim 12, wherein the first and second labelling substances are selected from the group consisting of radioisotopes, free radicals, fluorescent molecules, luminescent molecules, bacteriophages, enzymes, coenzymes and enzyme inhibitors.

14. A method as claimed in claim 13, wherein the labelling substances are radioisotopes.

15. A method as claimed in claim 12 wherein the ligand is selected from the group consisting of IgE, IgG, IgA, IgM and IgD, and the binding component is selected from the group consisting of, respectively, anti-IgE, anti-IgG, anti-IgA, anti-IgM and anti-IgD.

16. A method as claimed in claim 15 wherein the ligand is IgE.

17. A method as claimed in claim 15 wherein the binding component is anti-IgE.

18. In a specific binding assay inhibition method for determining the potency of an allergen extract which involves the binding of IgE and a labelled constituent which is a conjugate of a first labelling substance and anti-IgE, and includes the steps of forming a solid-phase activated substrate which has attached thereto a product which is allergen-IgE-labelled constituent, such that as the amount of soluble allergen added is increased, the amount of IgE bound to the solid-phase allergen decreases, the improvement which comprises the steps of:
(a) determining the binding capacity of the activated substrate-allergen and selecting a working dilution of the IgE which is less than the concentration capable of saturating the activated substrate;
(b) reacting IgE with a second labelling substance which is different then the first labelling substance used in the labelled constituent, for a time sufficient to label the IgE, whereby the labelled IgE can be distinguished from the labelled constituent;
(c) incubating activated substrates with anti-light chain antibodies, the labelled IgE and the labelled constituent under reaction conditions which are substantially the same as the reaction conditions used to form the allergen-IgE-labelled constituent;
(d) determining the amounts of labelled IgE capable of binding to various amounts of the labelled constituent, in terms of a standard IgE reference substance; and
(e) determining the IgE protein present in the allergen-IgE-labelled constituent product by reference to the relationship determined in step (d), whereby the amount of IgE inhibited by the soluble allergen is determined.

19. A method as claimed in claim 18 wherein the labelling substances are selected from the group consisting of radioisotopes, free radicals, fluorescent molecules, luminescent molecules, bacteriophages, enzymes, co-enzymes and enzyme inhibitors.

20. A method as claimed in claim 19 wherein the labelling substances are radioisotopes.

21. A method as claimed in claim 18 wherein the IgE is labelled with Na$^{131}$I and the anti-IgE is labelled with Na$^{125}$I.

22. A method as claimed in claim 18 wherein the standard IgE reference material is World Health Organization IgE.

23. A method as claimed in claim 18 wherein the amount of IgE protein present in the labelled IgE is determined by double antibody competitive inhibition of the IgE reference material.

24. In a specific binding assay inhibition method for determining the potency of an allergen extract which involves the binding of IgE and a radiolabelled constituent which is a conjugate of a first radio-isotope and anti-IgE, and includes the steps of forming a solid-phase activated substrate which has attached thereto a product which is allergen-IgE-anti-IgE, such that as the amount of soluble allergen added is increased, the amount of IgE bound to the solid-phase allergen decreases, the improvement which comprises the steps of:
(a) determining the binding capacity of the activated substrate-allergen and selecting a working dilution of the IgE which is less than the concentration capable of saturating the activated substrate;
(b) reacting IgE with a radioisotope which is different than the first radioisotope, for a time sufficient to label the IgE, whereby the radiolabelled IgE can be distinguished from the radiolabelled constituent;
(c) incubating activated substrates with anti-light chain antibodies, the radiolabelled IgE and the radiolabelled constituent under reaction conditions which are substantially the same as the reaction conditions used to form the allergen-IgE-radiolabelled constituent;
(d) determining the amounts of radiolabelled IgE capable of binding to various amounts of the radiolabelled constituent, in terms of a standard IgE reference substance; and
(e) determining the amount of IgE present in the radiolabelled IgE by reference to the relationship determined in step (d), whereby the amount of IgE inhibited by the soluble allergen is determined.

* * * * *